(12) United States Patent
Koseoglu et al.

(10) Patent No.: US 11,433,379 B2
(45) Date of Patent: Sep. 6, 2022

(54) MODIFIED USY ZEOLITIC CATALYST FOR ISOMERIZATION OF ALKYLATED AROMATICS, AND METHOD FOR ISOMERIZATION OF ALKYLATED AROMATICS

(71) Applicant: SAUDI ARABIAN OIL COMPANY, Dhahran (SA)

(72) Inventors: Omer Refa Koseoglu, Dhahran (SA); Robert Peter Hodgkins, Dhahramn (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/160,069

(22) Filed: Jan. 27, 2021

(65) Prior Publication Data

US 2022/0234033 A1    Jul. 28, 2022

(51) Int. Cl.
| | |
|---|---|
| *C07C 5/27* | (2006.01) |
| *B01J 29/08* | (2006.01) |
| *B01J 37/00* | (2006.01) |
| *B01J 35/10* | (2006.01) |
| *B01J 29/89* | (2006.01) |
| *B01J 29/10* | (2006.01) |
| *B01J 29/16* | (2006.01) |
| *B01J 29/12* | (2006.01) |
| *B01J 37/10* | (2006.01) |
| *B01J 29/14* | (2006.01) |

(52) U.S. Cl.
CPC ......... *B01J 29/088* (2013.01); *B01J 29/084* (2013.01); *B01J 29/106* (2013.01); *B01J 29/126* (2013.01); *B01J 29/146* (2013.01); *B01J 29/166* (2013.01); *B01J 29/89* (2013.01); *B01J 35/1023* (2013.01); *B01J 37/0009* (2013.01); *B01J 37/10* (2013.01); *C07C 5/2729* (2013.01); *C07C 5/2732* (2013.01); *C07C 5/2735* (2013.01); *C07C 5/2737* (2013.01); *C07C 5/2754* (2013.01); B01J 2029/081 (2013.01); B01J 2229/36 (2013.01); C07B 2200/09 (2013.01); C07C 2529/06 (2013.01); C07C 2529/072 (2013.01); C07C 2529/076 (2013.01); C07C 2529/08 (2013.01); C07C 2529/10 (2013.01); C07C 2529/12 (2013.01); C07C 2529/14 (2013.01); C07C 2529/16 (2013.01); C07C 2529/89 (2013.01)

(58) Field of Classification Search
CPC ........ B01J 29/89; B01J 29/084; B01J 29/088; B01J 2029/081; B01J 29/106; B01J 29/126; B01J 29/146; B01J 29/166; B01J 2229/183; B01J 2229/36; B01J 37/10; C07C 5/2737; C07C 5/2729; C07C 5/2732; C07C 5/2735; C07C 5/2754; C07C 2529/08; C07C 2529/06; C07C 2529/072; C07C 2529/076; C07C 2529/89; C07C 2529/10; C07C 2529/12; C07C 2529/14; C07C 2529/16
USPC ................................. 585/477, 480, 481, 482
See application file for complete search history.

(56) References Cited

U.S. PATENT DOCUMENTS

| | | | |
|---|---|---|---|
| 3,792,100 | A | 2/1974 | Sonoda et al. |
| 4,366,135 | A | 12/1982 | Le Van Mao et al. |
| 4,836,911 | A | 6/1989 | Skeels et al. |
| 5,401,488 | A | 3/1995 | Skeels et al. |
| 9,221,036 | B2 | 12/2015 | Koseoglu et al. |
| 10,081,009 | B2 | 9/2018 | Koseoglu et al. |
| 10,293,332 | B2 | 5/2019 | Koseoglu et al. |
| 10,399,858 | B2 | 9/2019 | Dusselier et al. |
| 10,787,618 | B2 | 9/2020 | Koseoglu et al. |
| 2014/0190868 | A1* | 7/2014 | Koseoglu ............... B01J 23/882 208/58 |
| 2018/0126364 | A1 | 5/2018 | Dusselier et al. |
| 2019/0224653 | A1 | 7/2019 | Koseoglu et al. |
| 2021/0179949 | A1* | 6/2021 | Koseoglu .................. C07C 2/66 |

FOREIGN PATENT DOCUMENTS

GB        2155916 A    10/1985

OTHER PUBLICATIONS

Zeolites in Industrial Separation and Catalysis, Wiley-VCH Verlag GmbH & Co., 2010, edited by Santi Kulprathipanja (pp. 462-464 and 491-495).
Kang, et al., "Promotional effect of spilt-over hydrogen on m-xylene isomerization over NiS/Al2O3-USY," Spllover and Migration of Surface Species on Catalyst, 221-228.
Rakshe, et al., "Acidity and m-Xylene Isomerization Activity of Large Pore, Zirconium-Containing Alumino-silicate with BEA Structure," Journal of Catalysts, 188:252-260 (1999).
Ivanovna, et al., "Effect of temperature on ethanol conversion over the surface of Zr-modified zeolite ZSM-5," Catal. Sustain. Energy, 2:83-86 (2015).
Al-Khattaf et al. "The effect of Y-zeolite acidity on m-xylene transformation reactions." Journal of Molecular Catalysis A: Chemical 225.1 (2005): 117-124.
International Search Report and Written Opinion for corresponding International Patent Application No. PCT/US22/13977 dated May 17, 2022. 8 pages.

* cited by examiner

*Primary Examiner* — Elizabeth D Wood
(74) *Attorney, Agent, or Firm* — Leason Ellis LLP

(57) ABSTRACT

The present invention relates to a catalyst for isomerization of alkylated aromatics such as mixed xylenes, using xylene isomerization catalyst particles including post-framework modified USY zeolite in which zirconium atoms and/or titanium atoms and/or hafnium atoms form a part of a framework of an ultra-stable Y-type zeolite.

17 Claims, No Drawings

MODIFIED USY ZEOLITIC CATALYST FOR ISOMERIZATION OF ALKYLATED AROMATICS, AND METHOD FOR ISOMERIZATION OF ALKYLATED AROMATICS

RELATED APPLICATIONS

Not applicable.

BACKGROUND

Field of the Invention

The present disclosure relates to a catalyst for isomerization of alkylated aromatics such as mixed xylenes into particular xylene components, including one or more of para-xylene, ortho-xylene or meta-xylene, and a process for isomerization of alkylated aromatics.

Description of Related Art

Xylenes are particularly important aromatic products for the world market. Therefore, the growing demand for para-xylene has driven expansions of production capacities and the creation of new petrochemical plants. The para-xylene is used as a raw material for many petrochemical products such as purified terephthalic acids.

It is known in the petroleum refining and petrochemical industry to isomerize alkylated aromatics from one or more sources in a refinery into more desirable isomers. In a petrochemical complex, xylenes are recovered by separation of reformate in an aromatic recovery complex. For example, xylene isomerization processes are used to maximize the recovery of a particular xylene isomer from a mixture of C8 aromatic isomers, para-xylene, ortho-xylene, meta-xylene, and ethylbenzene or commonly called "mixed xylenes." The xylene isomerization process is often applied to para-xylene recovery. In certain operations xylene isomerization can be used to maximize the recovery of ortho-xylene or meta-xylene. In the case of para-xylene recovery, a mixed xylene feed is charged to a para-xylene separation unit where the para-xylene isomer is preferentially separated, for instance in an adsorption column. Raffinate from the para-xylene separation unit, substantially free of para-xylene, is passed to a xylene isomerization unit to convert said raffinate to an equilibrium mixture of xylenes including para-xylene. Ortho-xylene and meta-xylene are catalytically isomerized over an acidic catalyst, including zeolitic catalysts, to form para-xylenes. The xylene isomerization unit reestablishes an equilibrium distribution of xylene isomers by producing para-xylene from ortho- and meta-isomers. The effluent from the xylene isomerization unit is recycled back to the xylene adsorption unit for recovery of additional para-xylene. In this manner, the ortho-and meta-isomers are recycled to extinction.

There are generally two different types of reactions that occur in a xylene isomerization reactor. There are isomerization reactions, whereby ethyl-benzenes are converted to xylenes, and whereby and ortho-xylene and meta-xylene are converted to para-xylene. In addition, there are dealkylation reactions, whereby the alkyl group is cleaved from an aromatic ring, such as conversion of ethyl benzene to benzene.

Various catalyst materials have been used for xylene isomerization process. In certain arrangements, acidic catalyst systems are used, while in others, dual functionality catalysts are used. Acidic characteristics promote xylene isomerization and naphthene isomerization for ethylbenzene conversion. Various types of zeolites have been proposed and are in use commercially.

Given the importance of preparing select isomers from mixed alkylated aromatics, it is not surprising that there is a substantial literature on xylene isomerization.

U.S. Pat. No. 4,836,911 to Skeels et al. teaches crystalline zeolitic aluminosilicates of the zeolite Y type, having at least some of its original framework aluminum atoms replaced by extraneous silicon atoms.

U.S. Pat. No. 5,401,488 to Skeels et al. teaches crystalline microporous aluminosilicates of the zeolite Y, zeolite L, mordenite or zeolite LZ-202 types, prepared by extracting aluminum and substituting chromium and/or tin for extracted aluminum to give molecular sieve products containing framework chromium and/or tin atoms.

U.S. Pat. No. 10,399,858 to Dusselieret et al. teaches SSZ-39, having an AEI framework, using organic structure directing agents.

U.K. Pat. No. 2,155,916 to Pyke teaches crystalline aluminometallophosphates modified by isomorphous substitution within the aluminium phosphate of ions of other elements, for example silicon, vanadium, iron, manganese, magnesium, zinc, titanium and zirconium.

U.S. Pat. No. 4,366,135 to Le Van Mao et al. teaches zeolites formed by using an organic quaternary ammonium structure directing agent, (DEPP)OH, wherein Al and Si can be optionally replaced, at least partially, by Ga and Ge respectively.

Catalytic hydrocracking and xylene isomerization are different in purpose and products. In hydrocracking large molecules are broken ("cracked") into smaller ones. While isomerization reactions may occur as a side reaction, it is not the objective, and conditions and feedstocks are different. In xylene isomerization reactions the molecules are converted by intermolecular methyl-shift. The inventors wish to draw attention to U.S. Pat. Nos. 9,221,036, 10,081,009 and 10,293,332, incorporated by reference in their entireties. The '036, '009 and '332 patents teach, inter alia, hydrocracking catalysts in which a USY framework has been substituted, in part, by one or more of zirconium, titanium, and hafnium. In these catalysts, the metal (Ti, Zr, and/or Hf), substitutes for part of the aluminum in the aluminum/silica framework, and essentially become part of the framework. Processes for making these catalysts and their use, are all described in the '036, '009 and '332 patents. Zeolite based catalysts provide sufficient acidity to function in cracking, which are desirable in hydrocracking.

Given the different aims, and reagents, used in isomerization processes and hydrocracking, it is surprising that the active catalytic support material can be modified to become a xylene isomerization catalyst. Yet, this is the subject of the invention, which is elaborated upon in the disclosure which follows.

Despite the many advances in xylene isomerization processes and their catalysts, the industry is constantly seeking improved catalyst materials, particularly those with improved isomerization rates.

SUMMARY OF THE INVENTION

A method for isomerizing an alkylated aromatics feed including a mixed-xylene feed to produce preferred isomers (xylene isomerization) is provided using xylene isomerization catalysts comprising, consisting of, or consisting essentially of, catalyst particles containing an active catalytic material or support material formed of post-framework modified USY zeolite material in which a portion of aluminum atoms constituting a zeolite framework thereof is substituted with zirconium atoms and/or titanium atoms and/or hafnium atoms. In certain embodiments the alkylated aromatics feed contains ortho-xylene and/or meta-xylene, and in certain embodiments the alkylated aromatics feed contains relatively small amounts of para-xylene, for instance, 0.01-2 wt %.

In certain embodiments the xylene isomerization catalyst used in a xylene isomerization can include the active catalytic material or active support material of post-framework modified USY zeolite as the catalytic particles, or as a component of the catalytic particles. The particles containing the post-framework modified USY zeolite can be provided alone or in combination other with xylene isomerization catalyst particles effective for isomerization of an alkylated aromatics feed including a mixed-xylene feed. The post-framework modified USY zeolite component is used to form active catalytic material or active support material as is known, optionally in composition with an effective amount with an inorganic oxide component, and optionally including an additional active component.

The post-framework modified USY zeolite includes framework-substituted zeolite in which a part of aluminum atoms constituting a USY zeolite framework thereof that is substituted with zirconium atoms and/or titanium and/or hafnium atoms. In certain embodiments, the post-framework modified USY zeolite contains from 0.1-5.0 wt % zirconium atoms and/or titanium and/or hafnium atoms as calculated as the oxide basis. As shown herein, such catalysts possess high isomerization activity that is effective for production of xylene isomers.

In the isomerization catalytic composition including the post-framework modified USY zeolite component used herein, the USY zeolite component and/or the post-framework modified USY zeolite can be characterized by a crystal lattice constant of 2.430 to 2.450 nm, a specific surface area of about 600-900 m$^2$/g, and a molar ratio of $SiO_2$ to $Al_2O_3$ generally in the range of about 5:1 to about 100:1, in certain embodiments about 12:1 to about 100:1, and in additional embodiments about 25:1 to about 90:1. The "specific surface area" referred to supra relates to the modified zeolite itself, as do all of the other properties listed. The zeolite containing catalyst support has a specific surface area of 150-500 or 150-450 m$^2$/g.

Operating conditions for xylene isomerization reactions include, for example: a reaction temperature range of about 230-450° C., a pressure range of about 1-30 bars, and a liquid hourly space velocity range, on a fresh feed basis relative to the total quantity of xylene isomerization catalysts, of about 0.5-26 h$^{-1}$. The xylene isomerization reactions occur in the presence of added hydrogen, or in the absence of added hydrogen. The xylene isomerization reactions occur in the presence of added hydrogen, or in the absence of added hydrogen. In embodiments in which the xylene isomerization reactions occur in the presence of added hydrogen, a hydrogen to mixed-xylenes molar ratio is in the range of about 0.5:1-10:1.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments, and serve to explain principles and operations of the described and claimed aspects and embodiments.

DETAILED DESCRIPTION

The disclosure provides methods for isomerization of alkylated aromatics including mixed xylenes, using a xylene isomerization catalyst including, as an active catalytic material or active support material, of an ultra-stable Y (hereafter "USY") zeolite that has been framework substituted. In certain embodiments, the framework-substituted zeolite incorporates one or more of zirconium, titanium, and hafnium into its framework to form the post-framework modified USY zeolite. The post-framework modified USY zeolite as the active catalytic material or active support material which is included in the catalyst particles used in the process herein are made, essentially, by using the processes described in U.S. Pat. Nos. 9,221,036, 10,081,009 and 10,293,332, incorporated by reference in their entireties above.

Xylene isomerization catalysts in the process herein include the catalyst particles having post-framework modified USY zeolite material. These post-framework modified USY zeolite catalyst particles include the post-framework modified USY zeolite material alone, in combination with other zeolite materials, and/or in combination with an inorganic oxide component (for example, where the materials are coextruded or otherwise combined during the manufacture of the catalyst particles). In certain embodiments, the isomerization catalyst particles comprise the post-framework modified USY zeolite material formed as catalyst particles without binder or other zeolite materials. In certain embodiments, the isomerization catalyst particles comprise the post-framework modified USY zeolite material and a binder material formed as catalyst particles, wherein the post-framework modified USY zeolite material comprises about 2-99, 2-98, 2-80, 2-70, 20-99, 20-98, 20-80 or 20-70 wt % of the catalyst particles, with the remaining mass comprising the binder. In certain embodiments, the isomerization catalyst particles comprise the post-framework modified USY zeolite material and another zeolite material formed as catalyst particles, wherein the post-framework modified USY zeolite material comprises about 2-99, 2-98, 2-80, 2-70, 20-99, 20-98, 20-80 or 20-70 wt % of the catalyst particles, with the remaining mass comprising the other zeolite material. In certain embodiments, the isomerization catalyst particles comprise the post-framework modified USY zeolite material, a binder, and another zeolite material formed as catalyst particles, wherein the post-framework modified USY zeolite material comprises about 2-99, 2-98, 2-80, 2-70, 20-99, 20-98, 20-80 or 20-70 wt % of the catalyst particles, with the remaining mass comprising the binder and the other zeolite material.

The post-framework modified USY zeolite catalyst particles are used in a xylene isomerization reactor alone or in effective combination with one or more additional catalyst particles that are suitable for xylene isomerization, in certain embodiments particularly to enhance production of para-xylenes. These one or more additional catalyst particles can include one or more zeolitic materials including USY, AEL, AFI, ATO, Beta, ITH, MFI, MRE, MOR, MWW (including MCM-22 and SSZ-25), NES and/or TUN. In embodiments in which post-framework modified USY zeolite catalyst particles are used in combination with other xylene isomerization catalyst particles, the content of post-framework modified USY zeolite catalyst particles is about 1-100, 1-99, 1-80, 1-70, 2-100, 2-99, 2-80 or 2-70 wt % of the total mass of all xylene isomerization catalyst particles.

In certain embodiments a method for isomerization of alkyl aromatics hydrocarbons having eight or more carbon atoms per molecule in a hydrocarbon feed comprises reacting the hydrocarbon feed in the presence or absence of hydrogen, under isomerizing conditions, and in the presence of an effective amount of an isomerization catalyst composition including a post-framework modified USY zeolite catalyst particles, alone or in combination with other catalyst particles effective for isomerization of alkylated aromatics including mixed xylenes. In certain embodiments a method for isomerization of mixed xylenes in a hydrocarbon feed having predominantly ortho-xylene and meta-xylene comprises reacting the hydrocarbon feed in the presence or absence of hydrogen, under isomerizing conditions, and in the presence of an effective amount of post-framework modified USY zeolite catalyst particles.

The post-framework modified USY zeolite material included in the isomerization catalyst particles as described herein is an ultra-stable Y-type zeolite in which silicon atoms and aluminum atoms form a zeolite framework and in which a part of the aluminum atoms is substituted with zirconium atoms and/or titanium atoms and/or hafnium atoms. The post-framework modified USY zeolite component of the isomerization catalyst compositions for isomerizing alkylated aromatics including mixed xylenes generally contains one or more of Zr, Ti, and Hf, in an amount of from 0.1-5.0, 0.1-4.0, 0.1-3.0, 0.2-5.0, 0.2-4.0, 0.2-3.0, 0.3-5.0, 0.3-4.0 or 0.3-3.0 wt %, as calculated on their oxide basis (that is, $ZrO_2$, $TiO_2$ and/or $HfO_2$) and as measured relative to the mass of the post-framework modified USY zeolite component. In certain embodiments, the amounts of individual materials supplying Zr, Ti, and Hf can be less than 0.1, 0.2 or 0.3 wt %, but when combined, the total is at least 0.1, 0.2 or 0.3 wt %. It is appreciated by a person of skill in the art, that when the framework-substituted zeolite in the catalyst contains the zirconium atoms and the titanium atoms and/or the hafnium atoms described above, a mass ratio (in terms of oxides) of the zirconium atoms to the titanium atoms and/or the hafnium atoms is not specifically be restricted, and any ratio of zirconium or titanium or hafnium that is effective to carry out the isomerization process herein can be used.

In certain embodiments the post-framework modified USY zeolite is:

a framework-substituted zeolite in which a part of aluminum atoms forming a zeolite framework is substituted only with zirconium atoms, and is referred to as a "zirconium-substituted zeolite" or "Zr-USY";

a framework-substituted zeolite in which a part of aluminum atoms forming a zeolite framework is substituted only with titanium atoms, and is referred to as a "titanium-substituted zeolite" or "Ti-USY";

a framework-substituted zeolite in which a part of aluminum atoms forming a zeolite framework is substituted only with hafnium atoms, and is referred to as a "hafnium-substituted zeolite" or "Hf-USY";

a framework-substituted zeolite in which a part of aluminum atoms forming a zeolite framework is substituted only with zirconium atoms and titanium atoms, and is referred to as a "zirconium-titanium-substituted zeolite" or "Zr—Ti-USY";

a framework-substituted zeolite in which a part of aluminum atoms forming a zeolite framework is substituted only with hafnium atoms and titanium atoms, and is referred to as a "hafnium-titanium-substituted zeolite" or "Hf—Ti-USY";

a framework-substituted zeolite in which a part of aluminum atoms forming a zeolite framework is substituted only with zirconium atoms and hafnium atoms, and is referred to as a "zirconium-hafnium-substituted zeolite" or "Zr—Hf-USY"; and a framework-substituted zeolite in which a part of aluminum atoms forming a zeolite framework is substituted only with zirconium atoms, titanium and hafnium atoms, and is referred to as "zirconium-titanium-hafnium substituted zeolite" or "Zr—Ti-Hf-USY."

The presence of the zirconium atoms and/or titanium and/or hafnium atoms which are substituted for the aluminum atoms in the post-framework modified USY zeolite serve as constituents of the framework of the USY zeolite. Substitution can be verified by, for example, X-ray fluorescence, high frequency plasma emission spectrometry, atomic absorption spectrometry, ultraviolet-visible-near-infrared spectrophotometry (UV-Vis-NIR), Fourier transform infrared spectroscopy (FT-IR), and/or nuclear magnetic resonance spectrometry (NMR).

Zeolite Component

Ultra-stable Y-type zeolite is used as the raw materials for preparing the post-framework modified USY zeolite. USY-type zeolite refers to zeolite having a crystal lattice constant (UD) generally in the range of about 2.425-2.450 or 2.430-2.450 nm; a specific surface area generally in the range of about 600-900, 600-800, 650-900 or 650-800 $m^2/g$; a molar ratio of $SiO_2$ to $Al_2O_3$ generally in the range of about 5:1-100:1, 10:1-100:1, 20:1-100:1, 5:1-80:1, 10:1-80:1, 20:1-80:1, 25:1-100:1 or 25:1-80:1; and a pore volume of about 0.3-0.75, 0.4-0.75, 0.3-0.6 or 0.4-0.6 ml/g. For example, suitable zeolites are FAU framework (zeolite Y) having its micropore pore formed by a 12-membered ring when viewed along the [111] direction is 7.4×7.4 Å. The crystal lattice constant can be measured by reference to ASTM method D3942, Standard Test Method for Determination of the Unit Cell Dimension of a Faujasite-Type Zeolite. The specific surface area is a value determined by the BET (Brunauer-Emmett-Teller) method using nitrogen adsorption. The ultra-stable Y-type zeolite may be prepared by any method known in the art. This ultra-stable Y-type zeolite is subjected to post-framework modification as described herein to form post-framework modified USY zeolite catalyst particles.

In additional embodiments, the post-framework modified USY zeolite material is combined with another zeolitic material and optionally a binder material to form post-framework modified USY zeolite xylene isomerization catalyst particles. The other zeolitic material can include but is not limited to mordenite, ZSM-5, ZSM-11, ZSM-12, ZSM-22, ZSM-23, ZSM 35, beta-type, Y and USY (wherein this USY zeolitic component is not the same as the post-framework modified USY zeolite described herein). For example, these can be (FAU) framework, which includes USY, having a micropore size related to the 12-member ring when viewed along the [111] direction of 7.4×7.4 Å; (MFI) framework, which includes ZSM-5, having a micropore size related to the 10-member rings when viewed along the [100] and [010] directions of 5.5×5.1 Å and 5.6×5.3 Å, respectively; (MEL) framework, which includes ZSM-11, having a micropore size related to the 10-member ring when viewed along the [100] direction of 5.4×5.3 Å; (MTW) framework, which includes ZSM-12, having a micropore size related to the 12-member ring when viewed along the [010] direction of 5.6×6.0 Å; (TON) framework, which includes ZSM-12, having a micropore size related to the 10-member ring when viewed along the [001] direction of 4.6×5.7 Å; (MTT)

framework, which includes ZSM-23, having a micropore size related to the 10-member ring when viewed along the [001] direction of 4.5×5.2 Å; (FER) framework, which includes ZSM-35, having a micropore size related to the 10-member ring and 8-member ring when viewed along the [001] and [010] directions of 4.2×5.4 Å and 3.5×4.8 Å, respectively; and (*BEA) framework, which includes zeolite beta polymorph A, having a micropore size related to the 12-member rings when viewed along the [100] and [001] directions of 6.6×6.7 Å and 5.6×5.6 Å, respectively.

Inorganic Oxide Component

In certain embodiments, the post-framework modified USY zeolite xylene isomerization catalyst particles are formed of the post-framework modified USY zeolite material, optionally one or more other zeolitic materials, and an effective amount of one or more inorganic oxide components. The combination of materials is coextruded or otherwise combined during the manufacture of the catalyst particles.

The inorganic oxide component typically contains a substance serving as a granulating agent or a binder. Usually, a known substance can be used as a granulating agent or binder for the isomerization catalyst herein. As the inorganic oxide, a porous inorganic oxide used in isomerization catalyst compositions in the related art can be used. Examples thereof include alumina, silica, titania, silica-alumina, alumina-titania, alumina-zirconia, alumina-boria, phosphorus-alumina, silica-alumina-boria, phosphorus-alumina-boria, phosphorus-alumina-silica, silica-alumina-titania, and silica-alumina-zirconia. In certain embodiments of the process for isomerization of alkylated aromatics including mixed xylenes as described herein, an inorganic oxide component comprising alumina is used in the isomerization catalyst compositions.

The post-framework modified USY zeolite xylene isomerization catalyst particles, containing an inorganic oxide component (optionally with active components), generally have a surface area in the range of about 150-500, 150-450, 200-500, 200-450 or 300-450 m²/g, and a pore volume in the range of about 0.4-0.75, 0.4-0.65, 0.45-0.75 or 0.45-0.65 ml/g. The content of the post-framework modified USY zeolite component and the inorganic oxide component of the catalytic compositions used for isomerization of alkylated aromatics including mixed xylenes as described herein are appropriately determined according to the object. For example, the post-framework modified USY zeolite xylene isomerization catalyst particles can have a post-framework modified USY zeolite content of about 2-100, 2-90, 2-80, 2-70, 20-100, 20-90, 20-80 or 20-70 wt % (where 100% refers to no inorganic oxide component). When plural types of post-framework modified USY zeolite materials are used in post-framework modified USY zeolite xylene isomerization catalyst particles, they are used preferably in a proportion so that the sum of the different types of post-framework modified USY zeolite components is within the ranges herein.

Additional Active Component

In certain optional embodiments, the post-framework modified USY zeolite xylene isomerization catalyst particles (including the post-framework modified USY zeolite material alone or in combination with another zeolitic material and/or with an inorganic oxide component) also have impregnated therein an additional active component to enhance catalytic activity for isomerization of alkylated aromatics including mixed xylenes, The active component can include one or more metal components known in the art of mixed xylene isomerization, for example, one or more of platinum, palladium or rhenium or combinations thereof can be used as an additional active component. In certain embodiments nickel and/or molybdenum can be used. For ethylbenzene isomerization, platinum is known to provide the aromatics hydrogenation activity. For olefin saturation that is desired for xylene isomerization with ethylbenzene dealkylation, a platinum, palladium, nickel, molybdenum, rhenium or combinations thereof can be used as an additional active component. The additional active component in the case of noble metals is present in an amount from 0-2, 0-1, 0-0.5, 0-0.4, 0.01-2, 0.01-1, 0.01-1, 0.01-0.5, 0.01-0.4, 0.05-2, 0.05-1, 0.05-0.5, 0.05-0.4, 0.1-2, 0.1-1, 0.1-0.5 or 0.1-0.4 wt % in terms of the metal component (metal mass for noble metals) and based on the mass of the catalyst particles. The additional active component in the case of non-noble metals such as nickel and/or molybdenum is present in an amount from 0-40, 0-35, 0-30, 0-10, 0-5, 0-2, 0-1, 0-0.5, 0-0.4, 0.01-40, 0.01-35, 0.01-30, 0.01-10, 0.01-5, 0.01-2, 0.01-1, 0.01-1, 0.01-0.5, 0.01-0.4, 0.05-40, 0.05-35, 0.05-30, 0.05-10, 0.05-5, 0.05-2, 0.05-1, 0.05-0.5, 0.05-0.4, 0.1-40, 0.1-35, 0.1-30, 0.1-10, 0.1-5, 0.1-2, 0.1-1, 0.1-0.5 or 0.1-0.4 wt % in terms of the metal component (metal, oxide or sulfide mass) based on a mass of the catalyst particles.

Several methods may be used to add the active component(s) to the support, including but not limited to immersion (dipping), incipient wetness, and evaporative. In the most commonly used method, a calcined support is immersed in an excess of solution containing active metals or metal compounds. The solution fills the pores and is also adsorbed on the support surface, and excess solution is removed. In another method, impregnation is carried out using incipient wetness by tumbling or spraying the activated support with a volume of solution having a concentration of metal compound tailored to achieve the targeted metal level, equal to or slightly less than the pore volume of the support. The metal-loaded support is then dried and calcined. Metal oxides are formed in the process; the calcination step is also referred to as oxidation. In another method, evaporative impregnation, the support is saturated with water or with acid solution and immersed into the aqueous solution containing the metal compound. That compound subsequently diffuses into the pores of the support through the aqueous phase.

Framework Substitution of USY Zeolite

The post-framework modified USY zeolite xylene isomerization catalyst particles include the post-framework modified USY zeolite material that is framework-modified. "Framework-modified" means that a portion of the aluminum atoms within the USY zeolite framework are substituted with zirconium and/or titanium and/or hafnium atoms, as disclosed in U.S. Pat. Nos. 9,221,036, 10,081,009 and 10,293,332, incorporated by reference in their entireties above.

In certain embodiments, a post-framework modified USY zeolite material is produced by firing a USY zeolite having the properties described herein at about 500-700° C. A suspension is formed containing the fired USY zeolite, the suspension having a liquid/solid mass ratio of about 5-15. An inorganic acid or an organic acid is added so that a pH of the suspension is about <2.0. Subsequently a solution containing a zirconium compound and/or a titanium compound and/or a hafnium compound is mixed. The solution is neutralized with, for example, an aqueous ammonia, so that the pH of the mixed solution is about 7.

In one example of a production method for a suitable USY zeolite material, a Y-type zeolite (Na—Y) is exchanged of sodium ions with ammonium ions by a conventional method, for example: dispersing Y-type zeolite in water to prepare a suspension, adding ammonium sulfate thereto, washing the solid matter with water, washing it with an ammonium sulfate aqueous solution at temperature in the range of about 40-80° C., subsequently washing it with water at temperature in the range of about 40-95° C., and drying at about 100-180° C., for example in a time range of about 30 minutes to about 30 hours. Accordingly an ammonium-exchanged Y-type zeolite, $NH_4\text{-}^{50\ to\ 70}Y$ in which about 50-70 wt % of Na contained in the Y-type zeolite is substituted with $NH_4$. Subsequently, a hydrogen type Y-type zeolite (HY) is prepared by calcining the above ammonium-exchanged Y-type zeolite ($NH_4\text{-}^{50\ to\ 70}Y$) at about 500-800° C. for about 10 minutes to about 10 hours in, for example, a saturated vapor atmosphere. Then, an ammonium-exchanged Y-type zeolite ($NH_4\text{-}^{80\ to\ 97}Y$) in which about 80-97 wt % of Na contained in the initial Y-type zeolite (Na—Y) is ion-exchanged with $NH_4$ is obtained by dispersing the hydrogen type Y-type zeolite obtained above in water at a temperature of about 40-95° C. to prepare a suspension, adding ammonium sulfate thereto, then stirring the suspension at a temperature of about 40-95° C. for about 10 minutes to about 3 hours, further washing the solid matter with water a temperature of about 40-95° C., next washing it with an ammonium sulfate aqueous solution a temperature of about 40-95° C., subsequently washing it with water a temperature of about 40-80° C. and then drying it at about 100-180° C. for about 30 minutes to about 30 hours. In certain embodiments the final ammonium ion exchange rate is 90% or greater. The ammonium-exchanged Y zeolite ($NH_4\text{-}^{80\ to\ 97}Y$) thus obtained is calcined at about 500-700° C. for about 10 minutes to about 10 hours in, for example, a saturated vapor atmosphere. Accordingly a USY zeolite is prepared having the properties described herein.

In the method for producing USY zeolite used in the isomerization catalyst composition herein, extraskeletal aluminum (aluminum atoms which do not form part of the zeolite framework) can be removed from the ultra-stable Y-type zeolite raw material in order to obtain the USY zeolite. Extraskeletal aluminum can be removed by, for example, a method of dispersing the ultra-stable Y-type zeolite described above in water at a temperature of about 40-95° C. to prepare a suspension, adding sulfuric acid to the thus-formed suspension and stirring it for about 10 minutes to about 3 hours while maintaining the temperature at about 40-95° C. to thereby dissolve the extraskeletal aluminum. After dissolving the extraskeletal aluminum, the suspension is filtrated, and a residue on the filter is washed with purified water at about 40-95° C. and dried at a temperature of about 100-180° C. for about 3-30 hours, whereby an ultra-stable Y-type zeolite from which the extraskeletal aluminum is removed can be obtained.

In the method for producing the post-framework modified USY zeolite herein, the USY zeolite which is the raw material is calcined at a temperature of about 500-700, 500-650, 550-700 or 550-650° C. The time of calcining is typically not critical so long as the targeted post-framework modified USY zeolite is obtained, for instance, in a range of about 30 minutes to about 10 hours. In certain embodiments calcining occurs in air. If the calcining temperature is lower than about 500° C., the framework substitution amount of zirconium atoms and/or titanium atoms and/or hafnium atoms tends to be reduced; at calcining temperatures that exceed about 700° C., the specific surface area of the ultra-stable Y-type zeolite can be reduced, and a framework substitution amount of zirconium atoms and/or titanium atoms and/or hafnium atoms is thus reduced.

The calcined ultra-stable Y-type zeolite is suspended in water having a temperature of about 20-30° C. to form a suspension. With respect to the concentration of the suspension of the ultra-stable Y-type zeolite, the liquid/solid mass ratio is generally in the range of about 5:1-15:1, 5:1-12:1, 8:1-15:1 or 8:1-12:1.

Next, an inorganic acid or an organic acid is added thereto so that a pH of the suspension described above is controlled to a range of about <2.0, and subsequently a solution containing a zirconium compound and/or titanium compound and/or a hafnium compound is added and admixed. The thus mixed solution is neutralized (for example, to a pH of about 7.0-7.5), and dried (for example, at a temperature of about 80-180° C.), whereby the post-framework modified USY zeolite described above can be obtained.

The inorganic acid use can generally be sulfuric acid, nitric acid, hydrochloric acid and the like. In certain embodiments the selected inorganic acid is sulfuric acid or hydrochloric acid. Further, carboxylic acids can suitably be used as the organic acid described above. The quantity of inorganic acid or organic acid is not critical, so long as the pH of the suspension is controlled in the range of about <2.0. For example, a 0.5- to 4.0-fold molar amount, and in certain embodiments a 0.7- to 3.5-fold molar, amount based on an amount of $Al_2O_3$ in the ultra-stable Y-type zeolite, can be used, although these ranges are not critical.

Suitable zirconium compounds described above include one or more of zirconium sulfate, zirconium nitrate, zirconium chloride and the like. In certain embodiments zirconium sulfate and/or zirconium nitrate are selected. The quantity of the zirconium compound added is generally about 0.1-5.0, 0.1-4.0, 0.1-3.0, 0.2-5.0, 0.2-4.0, 0.2-3.0, 0.3-5.0, 0.3-4.0 or 0.3-3.0 wt %, as calculated on their oxide basis (that is, zirconium oxide) and as measured relative to the mass of the post-framework modified USY zeolite component. Addition of the zirconium compound in an amount of less than about 0.1 wt % fails to improve solid acid characteristics of the zeolite. The addition of the zirconium compound in an amount exceeding 5 wt % tends to cause clogging of pores of the zeolite. An aqueous solution of a zirconium compound prepared by dissolving the zirconium compound in water can be used as the zirconium compound.

Suitable titanium compounds include one or more of titanium sulfate, titanium acetate, titanium chloride, titanium nitrate, and titanium lactate. In certain embodiments titanium sulfate and/or titanium acetate are selected. The quantity of the titanium compound added is generally about 0.1-5.0, 0.1-4.0, 0.1-3.0, 0.2-5.0, 0.2-4.0, 0.2-3.0, 0.3-5.0, 0.3-4.0 or 0.3-3.0 wt %, as calculated on their oxide basis (that is, titanium oxide) and as measured relative to the mass of the post-framework modified USY zeolite component. Addition of the titanium compound in an amount of less than about 0.1 wt % fails to improve solid acid characteristics of the zeolite. The addition of the titanium compound in an amount exceeding 5 wt % tends to cause clogging of pores of the zeolite. An aqueous solution of a titanium compound prepared by dissolving the titanium compound in water can be used as the titanium compound.

Suitable hafnium compounds described above include one or more of hafnium chloride, hafnium nitrate, hafnium fluoride, hafnium bromide, hafnium oxalate and the like. In certain embodiments hafnium chloride and/or hafnium nitrate are selected. The quantity of the hafnium compound added is generally about 0.1-5.0, 0.1-4.0, 0.1-3.0, 0.2-5.0, 0.2-4.0, 0.2-3.0, 0.3-5.0, 0.3-4.0 or 0.3-3.0 wt %, as calculated on their oxide basis (that is, hafnium oxide) and as measured relative to the mass of the post-framework modified USY zeolite component. Addition of the hafnium compound in an amount of less than about 0.1 wt % fails to improve solid acid characteristics of the zeolite. The addition of the hafnium compound in an amount exceeding 5 wt % tends to cause clogging of pores of the zeolite. An aqueous solution of a hafnium compound prepared by dissolving the hafnium compound in water can be used as the hafnium compound.

A pH of the above suspension is controlled to about <2.0 to prevent a precipitate from being generated during mixing of the aqueous solution of the zirconium compound and/or the hafnium compound and/or the titanium compound with a suspension of the ultra-stable Y-type zeolite described above.

Mixing of the aqueous solution of the zirconium compound and/or the hafnium compound and/or the titanium compound with a suspension of the ultra-stable Y-type zeolite is, in certain embodiments, is conducted by gradually adding said aqueous solution to the suspension. After completion of addition of the aqueous solution described above to the suspension, the solution can be mixed by stirring at, for example, room temperature (about 25-35° C.) for about 3-5 hours. Further, after completion of the above-described mixing, the admixed solution is neutralized by adding an alkali compound such as aqueous ammonia and/or the like, so that a pH thereof is controlled to about 7.0-7.5, whereby the post-framework modified USY zeolite described herein is be obtained.

In this regard: when only the zirconium compound (or an aqueous solution thereof) is used as the compound (or an aqueous solution thereof) and added to the suspension described above, the post-framework modified USY zeolite (Zr-USY) in which zirconium atoms are substituted for a part of aluminum atoms forming the framework of the ultra-stable Y-type zeolite is formed; when only the titanium compound (or an aqueous solution thereof) is used, the post-framework modified USY zeolite (Ti-USY) in which titanium atoms are substituted for a part of aluminum atoms forming the framework of the ultra-stable Y-type zeolite is formed; when only the hafnium compound (or an aqueous solution thereof) is used, the post-framework modified USY zeolite (Hf-USY) in which hafnium atoms are substituted for a part of aluminum atoms forming the framework of the ultra-stable Y-type zeolite is formed; when the zirconium compound and the titanium compound (or aqueous solutions thereof) are used, the post-framework modified USY zeolite in the catalyst (Zr—Ti-USY) in which zirconium atoms and titanium atoms are substituted for a part of aluminum atoms forming the framework of the ultra-stable Y-type zeolite is formed; when the zirconium compound and the hafnium compound (or aqueous solutions thereof) are used, the post-framework modified USY zeolite in the catalyst (Zr—Hf-USY) in which zirconium atoms and hafnium atoms are substituted for a part of aluminum atoms forming the framework of the ultra-stable Y-type zeolite is formed; when the hafnium compound and the titanium compound (or aqueous solutions thereof) are used, the post-framework modified USY zeolite in the catalyst (Hf—Ti-USY) in which hafnium atoms and titanium atoms are substituted for a part of aluminum atoms forming the framework of the ultra-stable Y-type zeolite is formed; and when the zirconium compound, the titanium compound and the hafnium compound (or aqueous solutions thereof) are used, the post-framework modified USY zeolite in the catalyst (Zr—Ti-Hf-USY) in which zirconium atoms, titanium atoms and hafnium atoms are substituted for a part of aluminum atoms forming the framework of the ultra-stable Y-type zeolite is formed.

The resulting framework-substituted zeolite can be filtered, if desired, washed with water, and dried at about 80-180° C.; the mixture may be quasi-equilibrated with steam, for instance, at a temperature of from about 600-800° C. for about 10-20 hours.

Formation of Catalyst Particles

The post-framework modified USY zeolite xylene isomerization catalyst particles are formed using the post-framework modified USY zeolite material as a component in known processes for forming catalyst, for example, by mixing the components and forming them into the desired shapes, for example by extruding or otherwise forming particles, as the post-framework modified USY zeolite xylene isomerization catalyst particles. The post-framework modified USY zeolite material in the catalytic particles services as an active catalytic material or as an active support material. Optionally an additional active component is incorporated as is known in catalyst manufacturing using active support material formed with the post-framework modified USY zeolite material alone or in combination with an inorganic oxide component.

Isomerization of Mixed Xylenes Using the Herein Catalyst

The xylene isomerization process is used to maximize the recovery of a particular xylene isomer from a mixture of C8 aromatic isomers, para-xylene, ortho-xylene, meta-xylene, and ethylbenzene or commonly called "mixed xylenes." The xylene isomerization process is most often applied to para-xylene recovery, but it can also be used to maximize the recovery of ortho-xylene or meta-xylene. In the case of para-xylene recovery, a mixed xylene feed is charged to a para-xylene separation unit where the para-xylene isomer is preferentially separated. The raffinate from the para-xylene separation unit, almost entirely free of para-xylene, is then sent to the xylene isomerization unit. In certain embodiments feed to the xylene isomerization unit contains about 0-2.0, 0.01-2.0, 0-1.0, 0.01-1.0, 0-0.5 or 0.01-0.5 wt % para-xylene, for instance, due to inefficiencies in para-xylene separation.

The xylene isomerization unit reestablishes an equilibrium distribution of xylene isomers, by creating para-xylene from ortho-and meta-isomers. The effluent from the xylene isomerization unit is then recycled back to the xylene adsorption unit for recovery of additional para-xylene. In this way, the ortho-and meta-isomers are recycled to extinction. As for the catalyst used, there are two different types of catalysts used in the xylene isomerization process. Two reactions are taking place: isomerization of ethyl-benzene to xylenes and ortho and meta-xylenes to para-xylene; and dealkylation ethyl benzene to benzene.

An apparatus for the mixed-xylenes isomerization process in the present disclosure using the post-framework modified USY zeolite xylene isomerization catalyst particles is not particularly limited as long as the foregoing reactions are carried out. Various types of apparatuses may be used. In accordance with some embodiments, the process of the present disclosure may be conducted in a fixed-bed reactor, an ebullated-bed or slurry-bed or moving-bed reactors or CSTR or batch type reactors, and the like.

The mixed-xylenes feed used in the processes herein using the post-framework modified USY zeolite xylene isomerization catalyst particles include ortho-xylene and meta-xylene, in certain embodiments with very small amounts of para-xylene as discussed above. In some embodiments, the ortho-xylene and meta-xylene feed is obtained from an aromatic recovery complex, which processes aromatic rich feedstreams such as reformate, FCC naphtha, or pyrolysis gasoline.

Since reformate feeds usually contain a very low amount of sulfur, as they are typically subjected to desulfurization prior to reforming such that the resulting gasoline product contains an acceptable level of sulfur for compliance with current sulfur specification. Aromatic streams from other sources such as FCC naphtha and pyrolysis gasoline generally contain higher levels of impurities than reformate and therefore typically require feed pretreatment to remove contaminants, especially nitrogen (N) and sulfur (S) species. Removal of these species can be effectuated by conventional treatments such as fractionation, adsorption and/or hydrotreating/stripping. In some embodiments, the mixed-xylenes, ortho-xylene and meta-xylene, are within a hydrocarbon feed mixture that contains less than about 0.5, 0.05 or 0.005 ppm sulfur.

The process is conducted at conditions suitable for effectuating an ortho-xylene and meta-xylene isomerization reaction. The isomerization reaction can be carried-out in the presence of hydrogen or in the absence of hydrogen. A person of skill in the art can determine process parameter such as temperature and pressure to achieve the desired result.

Operating conditions for xylene isomerization reactions include, for example: a reaction temperature of about 230-450, 230-400, 230-325, 230-300, 230-290, 250-450, 250-400, 250-325, 250-300, 250-290, 300-450, 300-400, 300-350, 300-325, 350-450 or 350-400° C.; a pressure of about 1-30, 5-30, 10-30, 1-20, 5-20, 8-20, 10-20, 1-15, 5-15, 8-15 or 10-15 bars; a liquid hourly space velocity (LHSV), on a fresh feed basis relative to the total quantity of xylene isomerization catalysts, of about 0.5-26, 3-26, 0.5-20, 3-20, 0.5-12, 3-12, 0.5-10, 3-10, 0.5-8 or 3-8 $h^{-1}$; and a hydrogen to mixed-xylenes molar ratio (wherein "0" represents absence of added hydrogen) of about 0:1-10:1, 0:1-3:1, 0.5:1-10:1, 0.5:1-3:1, 0.8:1-10:1 or 0.8:1-3:1. In embodiments of xylene isomerization in which there is no added hydrogen, suitable reaction temperatures can be in the range, for example, of about 230-300, 230-290, 250-450, 250-300 or 250-290° C., with pressure and space velocity as noted above. During the reactions, ortho-xylene and/or meta-xylene molecules are converted to para-xylene molecules so that the isomerized reaction effluents contains an increased concentration of para-xylene relative to the feed, for instance by at least about 1, 1.3, 2, 3, 3.3, or 4.4 wt %.

Source of Mixed Xylenes

The source of the mixed xylenes can vary. In certain embodiments, mixed xylenes can be obtained from a catalytic reformer, where a stream rich in alkylated aromatics is separated from reformer products in an aromatics recovery complex. In other embodiments, other streams rich in alkylated aromatics can be passed to an aromatics recovery complex, for example derived from one or more of pyrolysis gasoline, bio derived oils, plastic pyrolysis derived oils, hydrotreated coker naphtha, FCC naphtha.

Catalytic reformers are used in refineries to produce reformate, which itself is used as an aromatic rich gasoline blending fraction, or is used as feedstock to produce aromatics, also referred to as benzene, toluene, and xylene (BTX). Due to stringent fuel specifications implemented or being implemented worldwide, for example requiring less than 35 volume % (V %) aromatics and less than 1 V % benzene in gasoline, the reformate fraction is further treated to reduce its aromatics content. Treatment options available include benzene hydrogenation and aromatics extraction. In benzene hydrogenation, the reformate is selectively hydrogenated to reduce the benzene content, and the total aromatics content is reduced by blending if needed. In aromatics extraction, the reformate is sent to an aromatic complex to extract the aromatics, such as benzene, toluene and xylenes, which have a premium chemical value, and to produce an aromatics and benzene free gasoline blending component. The aromatic complex also produces a reject stream or bottoms stream that is very heavy (boiling in the range of about 100-350° C.), which is not suitable as a gasoline blending component.

In some catalytic reforming processes, a naphtha stream is first hydrotreated in hydrotreating unit to produce a hydrotreated naphtha stream. A hydrotreating unit operates under suitable conditions of, for instance, temperature, pressure, hydrogen partial pressure, LHSV, and catalyst selection and loading, which are effective to remove at least enough sulfur and nitrogen to meet requisite product specifications. For instance, hydrotreating in conventional naphtha reforming systems generally occurs under relatively mild conditions that are effective to remove sulfur and nitrogen to less than 0.5 ppmw levels. The hydrotreated naphtha stream is reformed in reforming unit to produce a gasoline reformate product stream. In general, the operating conditions for reforming unit include a temperature in the range of from about 400-600, 400-550, 430-600 or 430-550° C.; a pressure in the range of from about 1-50 or 1-20 bars; a LHSV, on a fresh feed basis relative to the reforming catalysts, in the range of from about 0.5-5 or 0.5-2 $h^{-1}$, and a hydrogen to hydrocarbon feed ratio of from 1:1-50:1 or 1:1-30:1 The reformate is typically sent to a gasoline pool to be blended with other gasoline components to meet the required specifications.

A typical gasoline blending pool includes C4 and heavier hydrocarbons having boiling points of less than about 180-205° C. In the catalytic reforming process, paraffins and naphthenes are restructured to produce isomerized paraffins and aromatics of relatively higher octane numbers. Catalytic reforming converts low octane n-paraffins to i-paraffins and naphthenes. Naphthenes are converted to higher octane aromatics. The aromatics are left essentially unchanged or some may be hydrogenated to form naphthenes due to reverse reactions taking place in the presence of hydrogen.

The reactions involved in catalytic reforming are commonly grouped into the four categories of cracking, dehydrocyclization, dehydrogenation and isomerization. A particular hydrocarbon/naphtha feed molecule may undergo more than one category of reaction and/or may form more than one product.

An effective quantity of reforming catalyst is provided. Such catalysts include mono-functional or bi-functional reforming catalysts, which generally contain one or more active metal component of metals or metal compounds (oxides or sulfides) selected from the Periodic Table of the Elements IUPAC Groups 8-10. A bi-functional catalyst has both metal sites and acidic sites. In certain embodiments, the active metal component can include one or more of Pt, Re, Au, Pd, Ge, Ni, Ag, Sn, Ir or halides. The active metal component is typically deposited or otherwise incorporated on a support, such as amorphous alumina, amorphous silica alumina, zeolites, or combinations thereof. In certain embodiments, effective reforming catalysts including IUPAC Group 8 metals of the Periodic Table, including precious metals such as Pt or Pt-alloy active metal components, which are supported on alumina, silica or silica-alumina. The hydrocarbon/naphtha feed composition, the impurities present therein, and the desired products will determine such process parameters as choice of catalyst(s), process type, and the like. Types of chemical reactions can be targeted by a selection of catalyst or operating conditions known to those of ordinary skill in the art to influence both the yield and selectivity of conversion of paraffinic and naphthenic hydrocarbon precursors to particular aromatic hydrocarbon structures.

The hydrocarbon/naphtha feed composition, the impurities present therein, and the desired products determine process parameters including selection of catalyst(s), process type and the like. Types of chemical reactions can be targeted by a selection of catalyst and/or operating conditions to influence both the yield and selectivity of conversion of paraffinic and naphthenic hydrocarbon precursors to particular aromatic hydrocarbon structures.

There are several types of catalytic reforming process configurations that carry out the reforming reactions, and differ mainly regarding regeneration of the reforming catalyst to remove coke formed during reaction. Catalyst regeneration, which involves combusting coke formed on catalyst particles in the presence of oxygen, includes a semi-regenerative process, cyclic regeneration, and continuous regeneration. Semi-regeneration is the simplest configuration, and the entire unit, which can include plural reactors in the series, is shut-down for regeneration of catalyst in all reactors. Cyclic configurations utilize an additional parallel reactor to permit one reactor at a time to be taken off-line for regeneration while the others remain in service in a swing mode of operation. Continuous catalyst regeneration configurations, which are the most complex, provide for essentially uninterrupted operation by catalyst removal, regeneration and replacement. While continuous catalyst regeneration configurations include the ability to increase the severity of the operating conditions due to higher catalyst activity, the associated capital investment is necessarily higher.

The reformate from a catalytic reforming unit is usually sent to an aromatics recovery complex where it undergoes several processing steps in order to recover high value products such as xylenes and benzene, and to convert lower value products such as toluene into higher value products. For example, the aromatics present in the reformate are usually separated into different fractions by carbon number, such as benzene, toluene, xylenes, and ethylbenzene, etc. The C8 fraction is then subjected to a processing scheme to make more high value para-xylene. Para-xylene is usually recovered in high purity from the C8 fraction by separating the para-xylene from the ortho-xylene, meta-xylene, and ethylbenzene using selective adsorption or crystallization. The ortho-xylene and meta-xylene remaining from the para-xylene separation are isomerized to produce an equilibrium mixture of xylenes. The ethylbenzene is isomerized into xylenes or is dealkylated to benzene and ethane. The para-xylene is then separated from the ortho-xylene and the meta-xylene using adsorption or crystallization and the para-xylene-depleted-stream is recycled to extinction to the isomerization unit and then to the para-xylene recovery unit until all of the ortho-xylene and meta-xylene are converted to para-xylene and recovered. In accordance with an embodiment, the isomerization unit includes an effective amount of an isomerization catalyst composition including the post-framework modified USY zeolite.

Toluene is recovered as a separate fraction, and then may be converted into higher value products, for example benzene in addition to or alternative to xylenes. One toluene conversion process involves the disproportionation of toluene to produce additional benzene and xylenes. Another process involves the hydrodealkylation of toluene to produce benzene. Both toluene disproportionation and toluene hydrodealkylation result in the formation of benzene, and in certain embodiments it is desirable that the toluene conversion does not result in the formation of significant quantities of benzene.

EXAMPLES

Example 1

First, 50.0 kg of a NaY zeolite (hereinafter, also referred to as "NaY") having a $SiO_2/Al_2O_3$ molar ratio of 5.2, a unit cell dimension (UD) of 2.466 nm, a specific surface area (SA) of 720 m$^2$/g, and a $Na_2O$ content of 13.0% by mass was suspended in 500 liter (hereinafter, also expressed as "L") of water having a temperature of 60° C. Then, 14.0 kg of ammonium sulfate was added thereto. The resulting suspension was stirred at 70° C. for 1 hour and filtered. The resulting solid was washed with water. Then the solid was washed with an ammonium sulfate solution of 14.0 kg of ammonium sulfate dissolved in 500 L of water having a temperature of 60° C., washed with 500 L of water having a temperature of 60° C., dried at 130° C. for 20 hours, thereby affording about 45 kg of a Y zeolite ($NH_4$ $^{65}$Y) in which 65% of sodium (Na) contained in NaY was ion-exchanged with ammonium ion ($NH_{41}$). The content of $Na_2O$ in $NH_4$ $^{65}$Y was 4.5% by mass.

$NH_4$ $^{65}$Y 40 kg was fired in a saturated water vapor atmosphere at 670° C. for 1 hour to form a hydrogen-Y zeolite (HY). HY was suspended in 400 L of water having a temperature of 60° C. Then 49.0 kg of ammonium sulfate was added thereto. The resulting mixture was stirred at 90° C. for 1 hour and washed with 200 L of water having a temperature of 60° C. The mixture was then dried at 130° C. for 20 hours, thereby affording about 37 kg of a Y zeolite ($NH_4$ $^{95}$Y) in which 95% of Na contained in the initial NaY was ion-exchanged with $NH_4$. $NH_4$ $^{95}$Y 33.03 kg was fired in a saturated water vapor atmosphere at 650° C., for 1 hour, thereby affording about 15 kg of a ultra stable Y zeolite (hereinafter, also referred to as "USY(a)") having a $SiO_2/Al_2O_3$ molar ratio of 5.2 and a $Na_2O$ content of 0.60% by mass.

Next, 26.0 kg of this USY(a) was suspended in 260 L of water having a temperature of 60° C. After 61.0 kg of 25% sulfuric acid by mass was gradually added to the suspension, the suspension was stirred at 70° C. for 1 hour. The suspension was filtered. The resulting solid was washed with 260 liter of deionized water having a temperature of 60° C. and dried 130° C. for 20 hours, thereby affording a ultra stable Y-type zeolite (hereinafter, also referred to as "USY(b)").

USY (b) was fired at 600° C. for 1 hour, thereby affording about 17 kg of ultra stable Y-type zeolite (hereinafter, also referred to as "USY").

Example 2

1 kg of USY obtained in Example 1 was suspended in 10 L of water at 25° C., and the pH of the solution was adjusted to 1.6 by sulfuric acid of 25% by mass. Titanyl sulfate of 33% by mass (60 g) was added and mixed, and the suspension was stirred at room temperature for 3 hours. Then, the pH was adjusted to 7.2 by adding aqueous ammonia of 15% by mass, and the suspension was stirred at room temperature for 1 hour and then filtrated. The resulting solid obtained was washed with 10 L of water and dried at 130° C., for 20 hours to obtain about 1 kg of a titanium-substituted type zeolite (hereinafter also referred to as "Ti-USY").

Example 3

First, 1 kg of USY obtained in Example 1 was suspended in 10 L of water at 25° C. The pH of the solution was adjusted to 1.6 by sulfuric acid of 25% by mass. Then 86 g of a solution containing 18% zirconium sulfate by mass was added thereto. The resulting mixture was stirred for 3 hours at room temperature. Then the pH was adjusted to 7.2 with 15% aqueous ammonia by mass. After the mixture was stirred for 1 hour at room temperature, the mixture was filtered. The resulting solid was washed with 10 L of water and dried at 130° C. for 20 hours, thereby affording about 1 kg of a zirconium-substituted zeolite (hereinafter also referred to as "Zr-USY").

Example 4

1 kg of USY obtained in Example 1 was suspended in 10 L of water at 25° C., and the pH of the solution was adjusted to 1.6 by sulfuric acid of 25% by mass. Zirconium sulfate of 18% by mass (86 g) and titanyl sulfate of 33% by mass (60 g) were added and mixed, and the suspension was stirred at room temperature for 3 hours. Then, the pH was adjusted to 7.2 by adding 15% by mass aqueous ammonia, and the suspension was stirred at room temperature for 1 hour and then filtered. A matter obtained was washed with 10 L of water and dried at 130° C. for 20 hours to obtain about 1 kg of a zirconium/titanium-substituted type zeolite (hereinafter referred to as "Ti—Zr-USY").

Example 5

2 kg of USY(a) obtained in Example 1 was suspended in 20 L of water at 60° C. 3.7 kg of sulfuric acid of 25% by mass was gradually added to the suspension and then stirred at 70° C. for one hour to dissolve extraskeletal aluminum. Then, the suspension was filtrated, and a matter obtained was washed with 20 liter of purified water at 60° C. and dried at 130° C. for 20 hours to obtain an ultra stable Y-type zeolite (hereinafter referred to as "USY(c)").

USY(c) thus obtained was calcined at 600° C. for 1 hour to obtain about 1.5 kg of an ultra stable Y-type zeolite (hereinafter referred to as "USY(d)").

1 kg of USY(d) thus obtained was suspended in 10 L of water of 25° C., and a pH of the solution was adjusted to 1.6 by sulfuric acid of 25% by mass. Zirconium sulfate of 18% by mass (86 g) and titanyl sulfate of 33% by mass (60 g) were added and mixed, and the suspension was stirred at room temperature for 3 hours. Then, the pH was adjusted to 7.2 by aqueous ammonia of 15% by mass, and the suspension was stirred at room temperature for 1 hour and then filtrated. A matter obtained was washed with 10 L of water and dried at 130° C. for 20 hours to obtain about 1 kg of a zirconium-titanium-substituted type zeolite (hereinafter also referred to as "Ti,Zr-USY2").

Example 6

2 kg of USY(a) obtained in Example 1 was suspended in 20 L of water at 60° C. 5.7 kg of sulfuric acid of 25% by mass was gradually added to the suspension and then stirred at 70° C. for one hour to dissolve extraskeletal aluminum. Then, the suspension was filtrated, and a matter obtained was washed with 20 liter of purified water at 60° C. and dried at 130° C. for 20 hours to obtain an ultra stable Y-type zeolite (hereinafter referred to as "USY(e)").

USY(e) thus obtained was calcined at 600° C. for 1 hour to obtain about 1.5 kg of an ultra stable Y-type zeolite (hereinafter referred to as "USY(f)").

1 kg of USY(f) thus obtained was suspended in 10 L of water of 25° C., and a pH of the solution was adjusted to 1.6 by sulfuric acid of 25% by mass. Zirconium sulfate of 18% by mass (86 g) and titanyl sulfate of 33% by mass (60 g) were added and mixed, and the suspension was stirred at room temperature for 3 hours. Then, the pH was adjusted to 7.2 by aqueous ammonia of 15% by mass, and the suspension was stirred at room temperature for 1 hour and then filtrated. A matter obtained was washed with 10 L of water and dried at 130° C. for 20 hours to obtain about 1 kg of a zirconium-titanium-substituted type zeolite (hereinafter also referred to as "Ti,Zr-USY3").

Example 7

Relative reactivities for all the catalysts prepared as described in Examples 1-6 above are provided in Table 1. Tables 2A-2F show results of isomerization ortho-xylene. Reactions were carried out in a continuous flow fixed-bed reactor under atmospheric pressure at 260° C., in the absence of hydrogen and in an argon atmosphere, over the six different calcined catalysts in Table 1.

The method and system of the present invention have been described above; however, modifications will be apparent to those of ordinary skill in the art and the scope of protection for the invention is to be defined by the claims that follow.

TABLE 1

| Catalyst | *Relative Isomerization Rate | WHSV (hr$^{-1}$) | LHSV (hr$^{-1}$) |
| --- | --- | --- | --- |
| USY - Ex. 1 | 1.5 | 0.31 | 0.35 |
| Ti-USY - Ex. 2 | 6.9 | 1.05 | 1.19 |
| Zr-USY - Ex. 3 | 2.4 | 0.60 | 0.68 |
| Ti,Zr-USY1 - Ex. 4 | 8.4 | 0.99 | 1.13 |
| Ti,Zr-USY2 - Ex. 5 | 51.8 | 2.05 | 2.33 |
| Ti,Zr-USY3 - Ex. 6 | 1.0 | 0.26 | 0.30 |

*Relative Isomerization Rate is the rate of reaction the listed catalyst divided by the rate of reaction of Ti,Zr-USY3.

TABLE 2A

USY (Catalyst A)

| Name | Retention time (min) | Wt. % (after 65 min) |
| --- | --- | --- |
| Benzene | 4.64 | 0.02 |
| Toluene | 5.37 | 1.44 |
| meta-xylene | 6.11 | 0.14 |
| para-xylene | 6.16 | 4.49 |
| ortho-xylene | 6.56 | 91.82 |
| 1,3,5-trimethylbenzene | 7.05 | 0.3 |
| 1,2,4-trimethylbenzene | 7.45 | 1.6 |
| 1,2,3-trimethylbenzene | 8.08 | 0.18 |
| tetramethylbenzenes | 9.40 | 0.01 |

*Retention time is the time of elution using gas chromatography.

TABLE 2B

Ti-USY

| Name | Retention time (min) | Wt. % (after 65 min) |
|---|---|---|
| Benzene | 4.64 | 0.02 |
| Toluene | 5.37 | 1.34 |
| meta-xylene | 6.11 | 0.11 |
| para-xylene | 6.16 | 1.3 |
| ortho-xylene | 6.56 | 95 |
| 1,3,5-trimethylbenzene | 7.05 | 0.09 |
| 1,2,4-trimethylbenzene | 7.45 | 1.88 |
| 1,2,3-trimethylbenzene | 8.08 | 0.2 |
| tetramethylbenzenes | 9.40 | 0.04 |

TABLE 2C

Zr-USY

| Name | Retention time (min) | Wt. % (after 65 min) |
|---|---|---|
| Benzene | 4.64 | 0.02 |
| Toluene | 5.37 | 1.33 |
| meta-xylene | 6.11 | 0.09 |
| para-xylene | 6.16 | 2.08 |
| ortho-xylene | 6.56 | 94.44 |
| 1,3,5-trimethylbenzene | 7.05 | 0.16 |
| 1,2,4-trimethylbenzene | 7.45 | 1.67 |
| 1,2,3-trimethylbenzene | 8.08 | 0.18 |
| tetramethylbenzenes | 9.40 | 0.03 |

TABLE 2D

Ti-Zr-USY1

| Name | Retention time (min) | Wt. % (after 65 min) |
|---|---|---|
| Benzene | 4.64 | 0.02 |
| Toluene | 5.37 | 2.09 |
| meta-xylene | 6.11 | 0.16 |
| para-xylene | 6.16 | 2.09 |
| ortho-xylene | 6.56 | 92.11 |
| 1,3,5-trimethylbenzene | 7.05 | 0.18 |
| 1,2,4-trimethylbenzene | 7.45 | 2.96 |
| 1,2,3-trimethylbenzene | 8.08 | 0.32 |
| tetramethylbenzenes | 9.40 | 0.05 |

TABLE 2E

Ti-Zr-USY2

| Name | Retention time (min) | Wt. % (after 65 min) |
|---|---|---|
| Benzene | 4.64 | 0.03 |
| Toluene | 5.37 | 2.73 |
| meta-xylene | 6.11 | 0.34 |
| para-xylene | 6.16 | 3.39 |
| ortho-xylene | 6.56 | 89 |
| 1,3,5-trimethylbenzene | 7.05 | 0.4 |
| 1,2,4-trimethylbenzene | 7.45 | 3.6 |
| 1,2,3-trimethylbenzene | 8.08 | 0.41 |
| tetramethylbenzenes | 9.40 | 0.09 |

TABLE 2F

Ti-Zr-USY3

| Name | Retention time (min) | Wt. % (after 65 min) |
|---|---|---|
| Benzene | 4.64 | 0.02 |
| Toluene | 5.37 | 1.53 |
| meta-xylene | 6.11 | 0.1 |
| para-xylene | 6.16 | 2.11 |
| ortho-xylene | 6.56 | 93.95 |
| 1,3,5-trimethylbenzene | 7.05 | 0.11 |
| 1,2,4-trimethylbenzene | 7.45 | 1.93 |
| 1,2,3-trimethylbenzene | 8.08 | 0.21 |
| tetramethylbenzenes | 9.40 | 0.03 |

The invention claimed is:

1. A process for isomerization of a hydrocarbon feed comprising ortho-xylene and/or meta-xylene comprising contacting the hydrocarbon feed with isomerization catalyst particles containing a framework-substituted ultra-stable Y-type (USY) zeolite in which a portion of aluminum atoms constituting a zeolite framework thereof is substituted with zirconium atoms and/or titanium atoms and/or hafnium atoms, the framework-substituted USY zeolite being an active catalytic material or active support material, wherein the ortho-xylene and/or meta-xylene are converted to para-xylene.

2. The process according to claim 1, wherein said framework-substituted USY zeolite contains from 0.1 to 5 mass % zirconium and/or titanium and/or hafnium as calculated as the oxide basis.

3. The process according to claim 1, wherein said isomerization catalyst particles are formed of framework-substituted USY zeolite and an inorganic oxide material as a binder.

4. The process according to claim 3, wherein said inorganic oxide material is selected from the group consisting of alumina, silica, titania, silica-alumina, alumina-titania, alumina-zirconia, alumina-boria, phosphorus-alumina, silica-alumina-boria, phosphorus-alumina-boria, phosphorus-alumina-silica, silica-alumina-titania, and silica-alumina-zirconia.

5. The process according to claim 3, wherein said framework-substituted USY zeolite comprises about 2-99 wt % of the isomerization catalyst particles, wherein any remaining mass comprising the inorganic oxide material.

6. The process according to claim 1, wherein said isomerization catalyst particles are formed of framework-substituted USY zeolite and another zeolite material.

7. The process according to claim 6, wherein said framework-substituted USY zeolite comprises about 2-99 wt % of the isomerization catalyst particles, with the remaining mass comprising the other zeolite material.

8. The process according to claim 1, wherein said isomerization catalyst particles are formed of framework-substituted USY zeolite, another zeolite material and an inorganic oxide material as a binder.

9. The process according to claim 8, wherein said framework-substituted USY zeolite comprises about 2-99 wt % of the isomerization catalyst particles, with the remaining mass comprising the other zeolite material and the inorganic oxide material.

10. The process according to claim 1, wherein said framework-substituted USY zeolite is an active catalytic material support in the absence of an additional active component.

11. The process according to claim 1, wherein said framework-substituted USY zeolite is an active support material support, and wherein an additional active component is carried on said active support material.

12. The process according to claim 11, wherein said additional active component is selected from the group of metals consisting of platinum, palladium, rhenium, nickel and molybdenum.

13. The process according to claim 12, wherein said additional active component is selected from the group of metals consisting of platinum, palladium and rhenium, and wherein said active component is present in an amount from 0.01-2 wt % in terms of the mass of the metal component relative to the mass of the catalyst particles.

14. The process according to claim 12, wherein said additional active component is selected from the group of metals consisting of nickel and molybdenum, and wherein said active component is present in an amount from 0.01-40 wt % in terms of the mass of the metal component based on the mass of the catalyst particles.

15. The process according to claim 1, wherein contacting the hydrocarbon feed with the isomerization catalyst composition occurs at reaction temperature range of about 230-450° C., a pressure range of about 1-30 bars and a LHSV range, on a fresh feed basis relative to the isomerization catalysts, of about 0.5-26 $h^{-1}$.

16. The process according to claim 15, wherein contacting the hydrocarbon feed with the isomerization catalyst composition occurs in the absence of hydrogen.

17. The process according to claim 15, wherein contacting the hydrocarbon feed with the isomerization catalyst composition occurs in the presence of hydrogen at a hydrogen to mixed-xylenes molar ratio range of about 0.5:1 to 10:1.

* * * * *